(12) United States Patent
Congdon et al.

(10) Patent No.: US 11,399,835 B2
(45) Date of Patent: Aug. 2, 2022

(54) HEMOSTASIS CLIP REDUCED LENGTH DEPLOYMENT MECHANISM

(71) Applicant: Boston Scientific Scimed, Inc., Maple Grove, MN (US)

(72) Inventors: Daniel Congdon, Hudson, MA (US); Laurie A. Lehtinen, Boylston, MA (US); Alex Roberts, Newton, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 136 days.

(21) Appl. No.: 16/898,222

(22) Filed: Jun. 10, 2020

(65) Prior Publication Data

US 2020/0397437 A1 Dec. 24, 2020

Related U.S. Application Data

(60) Provisional application No. 62/863,320, filed on Jun. 19, 2019.

(51) Int. Cl.
*A61B 17/10* (2006.01)
*A61B 17/00* (2006.01)

(52) U.S. Cl.
CPC ........ *A61B 17/10* (2013.01); *A61B 17/00234* (2013.01); *A61B 2017/0034* (2013.01)

(58) Field of Classification Search
CPC .......... A61B 17/00234; A61B 17/0057; A61B 17/1227; A61B 17/1285; A61B 2017/0034; A61B 2017/00584; A61B 2017/00623; A61B 2090/037
See application file for complete search history.

(56) References Cited

U.S. PATENT DOCUMENTS

| 2002/0177861 | A1 | 11/2002 | Sugiyama et al. |
| 2018/0098771 | A1 | 4/2018 | King et al. |
| 2019/0159783 | A1* | 5/2019 | Lehtinen ............... A61B 17/122 |

FOREIGN PATENT DOCUMENTS

| CN | 108969050 | 12/2018 |
| WO | 2018/173474 | 9/2018 |

* cited by examiner

*Primary Examiner* — Mohamed G Gabr
(74) *Attorney, Agent, or Firm* — Fay Kaplun & Marcin, LLP

(57) ABSTRACT

A clipping device includes a clip including a capsule and a pair of clip arms movable between an open configuration and a closed configuration. A tension member includes a distal portion and a proximal portion, a pair of protrusions extending from opposing surfaces of the proximal portion to be received within openings extending through proximal ends of the clip arms, the proximal portion including a relief to define a pair of fingers separated from one another at proximal ends thereof. A yoke including a central portion including a recess formed at a distal end thereof, the recess sized and shaped to releasably receive the pair of fingers of the tension member, the pair of fingers configured to flex toward one another when a predetermined force is exerted thereon to release the pair of fingers from the recess and disengage the tension member from the yoke during deployment of the clip.

19 Claims, 4 Drawing Sheets

HEMOSTASIS CLIP REDUCED LENGTH DEPLOYMENT MECHANISM

PRIORITY CLAIM

The disclosure claims priority to U.S. Provisional Patent Application Ser. No. 62/863,320 filed Jun. 19, 2019; the disclosure of which is incorporated herewith by reference.

FIELD

The present disclosure relates to endoscopic devices and, in particular, relates to endoscopic clipping devices for treating tissue along the gastrointestinal tract.

BACKGROUND

During endoscopic gastrointestinal (GI) procedures, the patient may be at risk of perforation of a wall of the GI tract, or may require closure of the GI tract wall as part of the procedure. Hemostasis clips may be used for hemostasis of, for example, mucosal/sub-mucosal defects, bleeding ulcers, arteries, polyps, diverticula, along with closure of luminal tract perforations. Depending on the size of the defect, multiple clips may be required.

SUMMARY

The present disclosure relates to a clipping device, comprising a clip including a capsule extending longitudinally from a proximal end to a distal end and including a channel extending therethrough, and a pair of clip arms, proximal ends of which are slidably received within the channel to move the clip arms between an open configuration and a closed configuration. A bushing releasably couples the clip to a proximal portion of the device. A tension member includes a distal portion and a proximal portion, each of which are sized and shaped to be received between proximal ends of the clip arms, and a pair of protrusions extending from opposing surfaces of the proximal portion to be received within openings extending through proximal ends of the clip arms to maintain an alignment between the clip anus, the proximal portion including a relief extending longitudinally therealong to define a pair of fingers separated from one another at proximal ends thereof. A yoke includes a central portion sized and shaped to be received between the proximal ends of the clip arms, the central portion including a recess formed at a distal end thereof, the recess sized and shaped to releasably receive the pair of fingers of the tension member, the pair of fingers configured to flex toward one another when a predetermined force is exerted thereon to release the pair of fingers from the recess and disengage the tension member from the yoke during deployment of the clip. A control member extends through the proximal portion of the device from a proximal end to a distal end attached to the yoke for moving the clip arms between the open and closed configurations.

In an embodiment, an exterior surface of the pair of fingers may be rounded and the recess formed in the central portion may be correspondingly rounded so that the pair of fingers are retained within the recess until the predetermined force is exerted thereon.

In an embodiment, the proximal end of the capsule may include tabs biased radially inward to engage a corresponding structure of the bushing, the central portion of the yoke sized and shaped to move the tabs radially outward as the distal end of the control member is moved proximally past the proximal end of the capsule to deploy the clip from the proximal portion.

In an embodiment, the yoke may include a pair of overhangs extending distally from a proximal end of the central portion so that proximal ends of the clip arms are constrained between the central portion and the overhangs toward an unlocked configuration.

In an embodiment, the proximal ends of the clip arms may be biased radially outward so that, in the unlocked configuration, locking structures at the proximal ends of the clip arms are prevented from engaging corresponding locking features of the capsule.

In an embodiment, the locking structures may include locking tabs extending from proximal ends of the clip arms and the locking features of the capsule may include windows extending laterally through a wall thereof so that, when the proximal ends of the clip are released from the distal end of the control member, the locking tabs are received within the locking windows to lock the clip in the closed configuration.

In an embodiment, the clip arms may include engaging features configured to engage portion of the capsule such that, when the engaging features engage the capsule, the clip arms are prevented from moving further proximally relative to capsule and the predetermined force is exerted on the distal end of the control member.

The present disclosure also relates to a clipping device, comprising a clip including a capsule extending longitudinally from a proximal end to a distal end and including a channel extending therethrough, and a pair of clip arms, proximal ends of which are slidably received within the channel to move the clip arms between an open configuration and a closed configuration. A bushing releasably couples the clip to a proximal portion of the device. A control member extends through the proximal portion of the device from a proximal end to a distal end releasably coupled to the clip arms to move the clip between the open and closed configurations and a yoke is attached to the distal end of the control member for releasably coupling the control member to the clip arms. The yoke includes a central portion sized and shaped to be received between proximal ends of the clip arms, a pair of protrusions extending from opposing surfaces of the central portion to be received within openings extending through the proximal ends of the clip arms to maintain an alignment therebetween, and a pair of reliefs formed therein so that, when a predetermined force is exerted on the yoke, a portion of the yoke defined via the reliefs is separated from a remaining portion of the yoke to release the clip arms from the control member during deployment of the clip.

In an embodiment, the pair of reliefs may extend from the distal end of the central portion of the yoke along opposing sides of the protrusions to define a stress concentration neck along which the yoke is configured to separate during deployment of the clip.

In an embodiment, the pair of reliefs may extend through the protrusions proximate the opposing surfaces of the central portion so that, when the predetermined force is exerted thereon, the protrusions are sheared off to release the clip arms from the control member.

In an embodiment, the proximal end of the capsule may include tabs biased radially inward to engage a corresponding structure of the bushing, the central portion of the yoke sized and shaped to move the tabs radially outward as the distal end of the control member is moved proximally past the proximal end of the capsule to deploy the clip from the proximal portion.

In an embodiment, the yoke may include a pair of overhangs extending distally from a proximal end of the central portion so that proximal ends of the clip arms are constrained between the central portion and the overhangs toward an unlocked configuration.

In an embodiment, the proximal ends of the clip arms may be biased radially outward so that, in the unlocked configuration, locking structures at the proximal ends of the clip arms are prevented from engaging corresponding locking features of the capsule.

In an embodiment, the locking structures may include locking tabs extending from proximal ends of the clip arms and the locking features of the capsule may include windows extending laterally through a wall thereof so that, when the proximal ends of the clip are released from the distal end of the control member, the locking tabs are received within the locking windows to lock the clip in the closed configuration In an embodiment, the clip arms may include engaging features configured to engage portion of the capsule such that, when the engaging features engage the capsule, the clip arms are prevented from moving further proximally relative to capsule and the predetermined force is exerted on the distal end of the control member.

The present disclosure also relates to a method for treating target tissue. A clip device is inserted through a working channel of an endoscope to a target site within a body until a clip of the clip device extends distally past a distal end of the working channel. The clip device includes a capsule and a pair of clip arms slidably received therein, the pair of clip arms aligned relative to one another via a tension member including a distal portion and a proximal portion sized and shaped to be received between proximal ends of the clip arms, and a pair of protrusions extending from opposing surfaces of the proximal portion to be received within openings extending through proximal ends of the clip arms to maintain an alignment between the clip arms. The clip device is moved between an open configuration and a closed configuration via a control wire coupled to the clip arms, until selected target tissue is received between the distal ends. A distal end of the control wire is coupled to proximal ends of the clip arms via a yoke including a central portion received between the proximal ends of the clip arms, a pair of fingers of the proximal portion of the tension member releasably received within a recess of the central portion. The clip arms are drawn proximally into the capsule to move the clip toward the closed configuration to grip the target tissue between the clip arms. The clip is deployed from a proximal portion of the clip device by drawing the control member proximally relative to the capsule until a predetermined force is exerted on the pair of fingers via the yoke, causing the pair of fingers to flex toward one another to release the tension member from the yoke.

DETAILED DESCRIPTION

Figure 1:
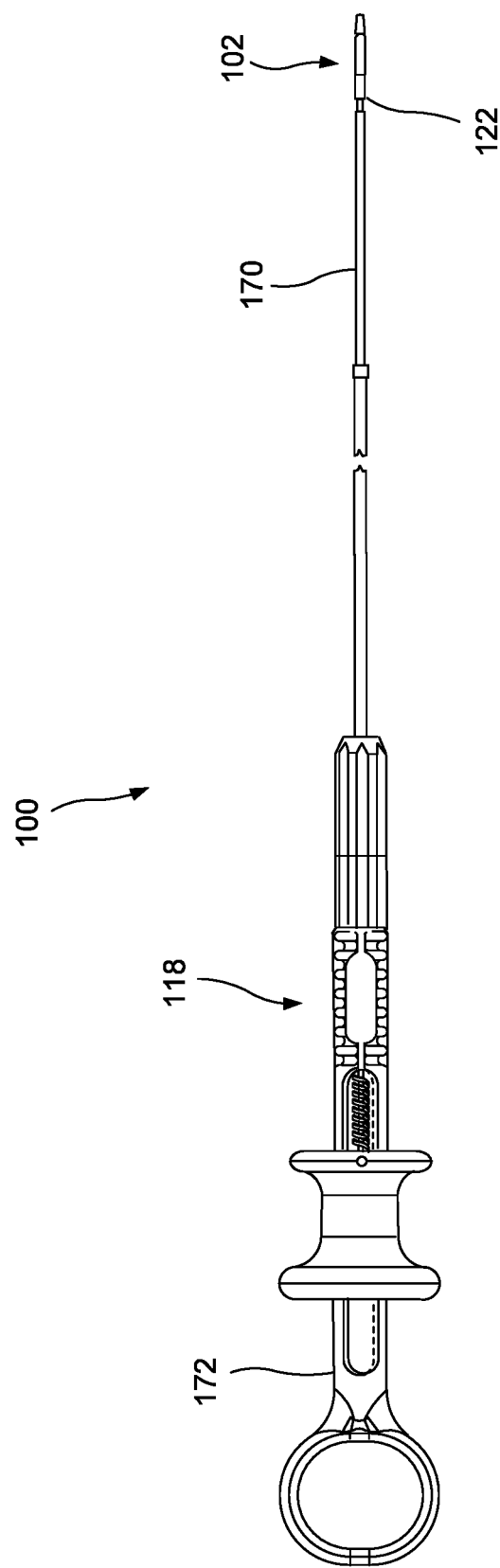
FIG. 1 shows a longitudinal side view of a clipping device according to an exemplary embodiment of the present disclosure.
Figure 2:
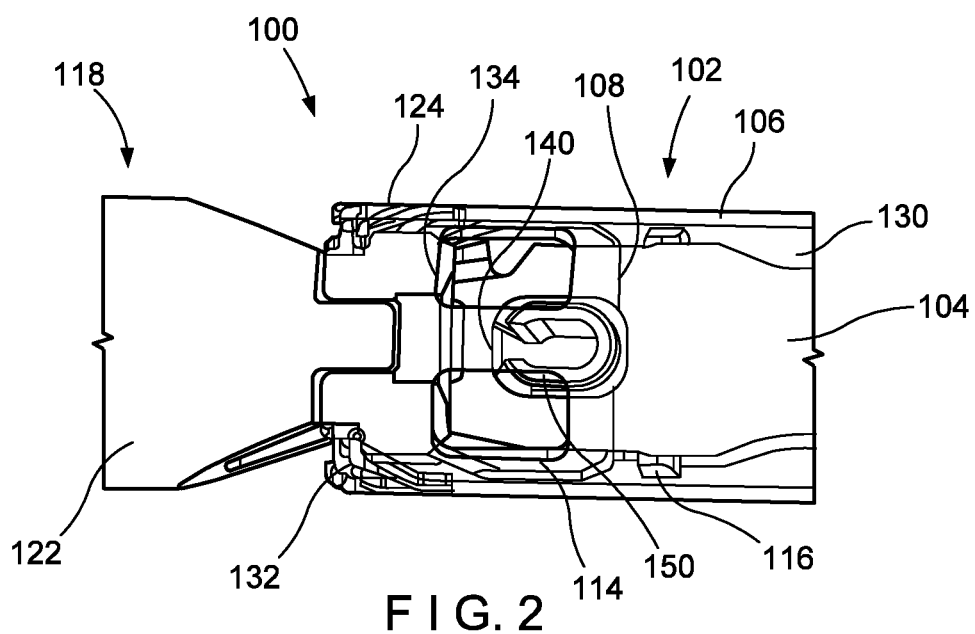
FIG. 2 shows a partially transparent longitudinal side view of a portion of the clipping device of FIG. 1.
Figure 3:
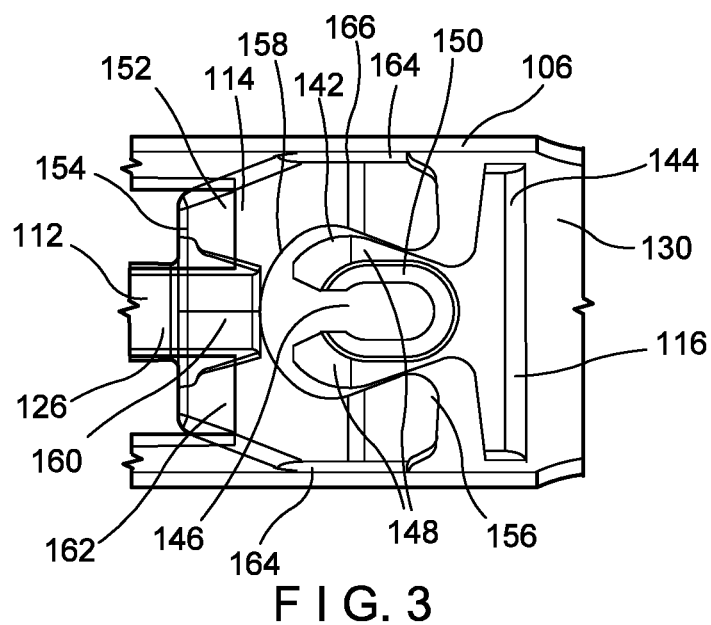
FIG. 3 shows a partially transparent longitudinal side view of a deployment mechanism of the clipping device of FIG. 1.
Figure 4:
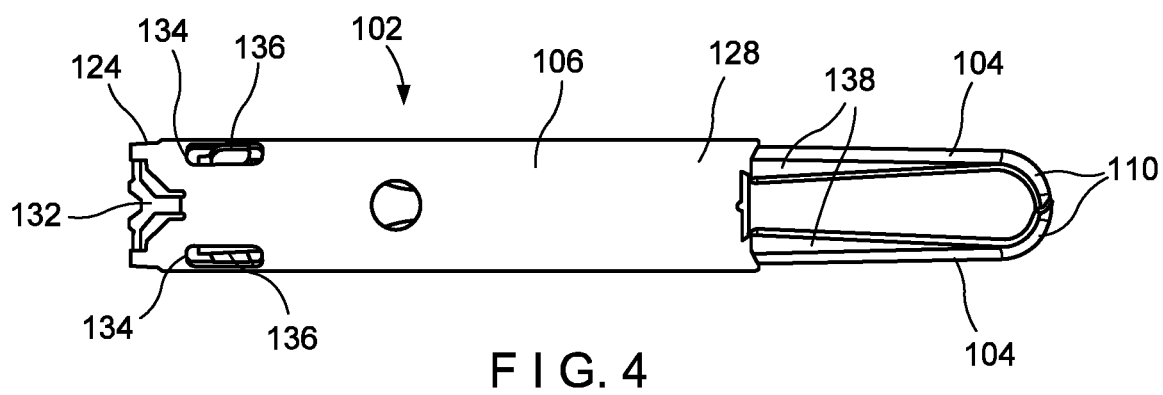
FIG. 4 shows a longitudinal side view of a deployed portion of the clipping device according to FIG. 1.

The present disclosure may be further understood with reference to the following description and the appended drawings, wherein like elements are referred to with the same reference numerals. The present disclosure is directed to an endoscopic clipping device for treating internal tissue perforations, defects and/or bleeds. In some embodiments, a shorter deployed clip may be preferred to improve visualization of a target site and to allow better maneuverability when placing multiple clips. Exemplary embodiments of the present disclosure describe a clipping device having a shortened deployment mechanism so that a length of the deployed clip is shortened compared to some current clips and which are configured to prevent the shedding parts of the clip into the body. A yoke portion of the deployment mechanism of may be configured to break and/or separate from a remaining portion of the deployment mechanism via one or more reliefs formed therealong. The separated yoke portion, which is connected to the distal end of a control member, is entirely separated and removed from the deployed clip during deployment and then removed from the body, as will be described in further detail below. It will be understood by those of skill in the art that the terms proximal and distal as used herein, are intended to refer to a direction toward and away from, respectively, a user of the device.

As shown in FIGS. 1-4, a clipping device 100 for treating tissue defects comprises a clip 102 including a pair of clip arms 104, proximal ends 108 of which are slidably received within a capsule 106 so that the clip 102 may move between an open configuration, in which distal ends 110 of the clip arms 104 are separated from one another, and a closed configuration, in which distal ends 110 are drawn toward one another. The clip arms 104 are moved between the open and the closed configurations via proximal and distal movement of a control member 112 that is coupled to the clip arms 104 via a yoke 114 and a tension member 116.

The tension member 116 is configured to maintain a desired alignment of the clip arms 104 relative to one another while the yoke 114, which is releasably coupled to the tension member 116, constrains proximal ends 108 of the clip arms 104 toward an unlocked configuration preventing the locking of the clip arms 104 in the capsule 106 until the clip 102 is deployed and locked in place over target tissue. The clip 102 is releasably coupled to a proximal portion 118 of the device 100, facilitating insertion of the clipping device 100 to a target site.

The proximal portion 118 includes a flexible elongate member 170 housing the control member 112 and connecting the clip 102 to a handle and/or actuator(s) 172 which, during use, remain outside the body accessible to a user to permit the user to control operation and movement of the device 100 between the open and closed configurations and to deploy the clip 102 over target tissue. The flexible elongate member 170 may be releasably coupled to the clip 102 via, for example, a bushing 122. The control member 112 extends through the elongate member from a proximal end connected to a portion of the handle member 172 to the distal end 126 which is connected to the yoke 114.

The capsule 106 extends from the proximal end 124 to a distal end 128 and includes a channel 130 extending therethrough. In one embodiment, the proximal end 124 is configured to be releasably coupled to the bushing 122 via, for example, tabs 132 that are crimped radially inward to engage a corresponding portion of the bushing 122. The capsule 106 also includes locking features formed in a capsule wall such as, for example, locking windows 134 that extend laterally through the capsule wall for engaging, for example, locking tabs 136 of the clip arm 104, as will be described in further detail below.

Each of the clip arms 104 extends from a proximal end 108 to its distal end 110. As described above, proximal portions of the clip arms 104 are slidably received within the channel 130 of the capsule 106. Specifically, the proximal end 108 of each of the clip arms 104 is slidably received within the channel 130 allowing the clip 102 to be moved between the open and closed configurations via manipulation of the control member 112. In one embodiment, the clip arms 104 are biased toward the open configuration so that, when advanced distally out of the capsule 106, the clip anus 104 move apart from one another into the open configuration under their natural bias. When the arms 104 are drawn proximally into the capsule 106, the clip arms 104 are constrained by the wall of the capsule 106 and drawn together into the closed position with the distal ends 110 adjacent one another. Those skilled in the art will understand that any number of other mechanisms for opening and closing the clip arms 104 may be employed.

The clip arms 104 of this embodiment also include engaging features 138 extending therefrom and configured to engage a portion of the capsule 106 so that, when the engaging features 138 engage the capsule 106, the clip arms 104 are prevented from being moved further proximally into the capsule 106. In one embodiment, the engaging features 138 extend laterally outward having a greater width than more proximal portions of the clip arms 104 that are sized to permit them to be drawn proximally into the capsule 106. Thus, as the clip arms 104 are drawn proximally into the capsule 106, the engaging features 138 abut a portion of a distal face 154 of the capsule 106. The engaging features 138 are positioned along the clip anus 104 so that, at the point where the engaging features 138 have engaged the capsule 106, the clip arms 104 have been drawn sufficiently proximally into the capsule 106 to draw the clip arms 104 together into the closed configuration. In one example, the engaging features 138 are configured as wings extending laterally from longitudinal edges of the clip arms 104.

Proximal ends 108 of the clip arms 104 include locking features such as, for example, locking tabs 136 extending therefrom. The proximal ends 108 of the clip arms 104, in this embodiment, are biased radially outward away from a centerline of the capsule 106 but, prior to deployment of the clip 102, are restrained by the yoke 114 and prevented from engaging the wall of the capsule 106. When the clip 102 is deployed, the control member 112 is released from the clip 102 via the yoke 114 and the locking tabs 136 are freed to spring radially outward into engagement with the locking windows 134, locking the clip arms 104 in the closed configuration over target tissue. The proximal ends 108 of the clip arms 104 of this embodiment also include openings 140 extending therethrough for receiving a portion of the tension member 116 therein to hold the clip arms 104 in a desired alignment relative to one another.

The tension member 116 is configured to be received between proximal ends 108 of the clip arms 104 and includes a proximal portion 142 extending proximally from a distal portion 144. The proximal portion 142 is sized and shaped to be received within a correspondingly sized and shaped portion of the yoke 114. The proximal portion 142 includes a relief 146 extending distally thereinto to define a pair of fingers 148 which may flex and/or deform toward one another to release the tension member 116 from the yoke 114 during deployment of the clip 102.

Each of the fingers 148 has an outwardly curved shape so that, together, the pairs of fingers 148 form a substantially rounded proximal portion 142 of the clip 102 to facilitate retention of the proximal portion 142 within the yoke 114 until separation (i.e., deployment) is desired. The fingers 148 include protrusions 150 extending from opposing surfaces thereof so that each protrusion 150 received within a corresponding one of the openings 140 of the clip arms 104 to maintain an alignment between the clip arms 104. Each protrusion 150 is sized and shaped to correspond to a shape of the openings 140 and, in one embodiment, has a substantially C-shaped cross-section so that each protrusion 150 extends along both fingers 148, allowing the fingers 148 to be released from the yoke 114. A width of the distal portion 144 in this embodiment substantially corresponds to a width (e.g., diameter) of the capsule 106 so that the tension member 116 is slidable within the channel 130 thereof.

The yoke 114 includes a central portion 152 sized and shaped to be received between proximal ends 108 of the clip arms 104 and overhangs 160 that constrain the proximal ends 108 of the clip arms 104 in an unlocked configuration in which the locking tabs 136 of the clip arms 104 are held out of engagement with the locking windows 134 of the capsule 106. The central portion 152 extends from the proximal end 154 attached to the distal end 126 of the control member 112 to a distal end 156. In one embodiment, the central portion 152 is defined via opposing surfaces 162, with each opposing surface 162 contacting a corresponding one of the proximal ends 108 of the clip arms 104, and lateral surfaces 164 connecting longitudinal edges 166 of the opposing surfaces 162 from the proximal end 154 to the distal end 156.

The overhangs 160 extend distally from the proximal end 154 along the opposing surfaces 162 so that each proximal end 108 is received between the central portion 152 and a corresponding one of the overhangs 160. The overhangs 160 thus hold the proximal ends 108 of the clip arms 104 at a position near a centerline of the capsule 106 out of engagement with the wall of the capsule to prevent the locking tabs 136 from engaging the locking windows 134 until the clip 102 is deployed.

A recess 158 extending proximally into the distal end 156 of the central portion 152 is sized and shaped to receive the proximal portion 142 of the tension member 116. In one embodiment, the recess 158 is substantially C-shaped to receive the curved fingers 148 of the proximal portion 142 therein. Corresponding curvatures of the recess 158 and the fingers 148 ensure retention of the fingers 148 within the recess 158 until it is desired that the yoke 114 and tension member 116 disengage one another. As described above, the pair of fingers 148 are designed to deform toward one another, when subjected to a predetermined force, to release the tension member 116 from the yoke 114. When the clip 102 is closed and the engaging features 138 of the clip arms 104 prevent further proximal motion of the clip anus 104 relative to the capsule 106, continued proximal force exerted on the control member 112 increases tension on the control member 112 until the predetermined force is applied at which point the yoke 114 is separated from the tension member 116.

A width of the central portion 152 substantially corresponds to a width (e.g., diameter) of the capsule 106 so that the central portion 152 is slidable within the channel 130 of the capsule 106 during movement of the clip arms 104 between the open and closed configurations. This also facilitates release of the capsule 106 from the bushing 122 during deployment. Upon separation of the yoke 114 from the tension member 116, the proximal ends 108 of the clip arms 104 are released from the overhangs 160 freeing the locking tabs 136 of the clip arms 104 to spring radially outward into engagement with the locking windows 134 of the capsule 106 locking the clip 102 in the closed configuration.

A user can then continue to exert proximal force on the control member 112 to moves the yoke 114 proximally past the proximal end 124 of the capsule 106 so that the lateral surfaces 162, which define the width of the central portion 152, push the inwardly crimped tabs 132 of the capsule 106 radially outward, away from the centerline of the capsule 106 disengaging the capsule 106 from the bushing 122 freeing the clip 102 from the proximal part 118 of the device 100 so that the clip 102 may be left in place clipped over the target tissue as the proximal part 118 of the device 100 is withdrawn from the body.

In one embodiment, the yoke 114 is drawn proximally into the bushing 122 so that the yoke 114 is removed from the body along with the proximal portion 118 of the device 100 so that no part of the device 100 is shed in the body and the only thing left in the body after withdrawal of the proximal portion 118 from the body is the deployed clip 102. In another embodiment, the yoke 114 may be drawn through the bushing 122 and into a flared distal end of the flexible elongate member 170 to similarly remove the yoke 114 from the body during withdrawal of the proximal portion 118.

According to an exemplary method utilizing the clipping device 100, the clip 102 is inserted through, for example, a working channel of an endoscope to a target site within a body while the handle member remains exterior to the body. The clip 102 is inserted through the working channel in the closed configuration. Once the clip 102 has reached the target site, the user advances the control member 112 distally to advance the clip arms 104 distally out of the capsule 106 freeing the clip arms 104 to move under their natural bias toward the open configuration so that target tissue may be received between the clip arms 104. The user may then operate the control member 112 to move the clip 102 between the open and closed configurations as desired until a target portion of tissue is positioned between the clip arms 104 as desired. The user then draws the control member 112 proximally (or advances the proximal portion 118 distally over the control member 112) so that, as the clip anus 104 are drawn into the capsule 106, the clip arms 104 are drawn toward one another to grip the target tissue between the distal ends 110 of the clip arms 104.

When the user is satisfied that the clip 102 is in a desired position gripping the target tissue, the user applies increasing proximally directed force to the control member 112 after the engaging features 138 have engaged the capsule 106, as described above, until the fingers 148 of the tension member 116 flex/deform toward one another and are released from the recess 158 of the yoke 114. As the yoke 114 is separated from the tension member 116, the proximal ends 108 of the clip arms 104 are released from the overhangs 160, freeing the proximal ends 108 to spring outward away from the centerline of the capsule 106 until the locking tabs 136 engage the locking windows 134 of the capsule 106 locking the clip 102 in the closed configuration.

The user then draws the control member 112 further proximally relative to the capsule 106 until the distal end 114 engages the tabs 132 pushing them outward to disengage the capsule 106 from the bushing 122 and freeing the clip 102 from the proximal portion 118 of the device 100 leaving the clip 102 coupled to the target tissue. The control member 112 may then be withdrawn proximally until the yoke 114 is received within the bushing 122 and withdraws the proximal portion 118 with the entire the control member 112 received therein from the body.

The combined tension member 116 and yoke 114 of this embodiment may have a length of approximately 2 mm compared to some conventional clip designs, which have a combined deployment mechanism length of approximately 6 to 7 mm. The relatively shortened deployment mechanism results in a correspondingly reduced capsule 106 length of approximately 7 to 8 mm, and in one particular embodiment, of approximately 7.5 mm. The capsule 106 of this embodiment may be substantially shorter than some conventional clips, which may have lengths ranging from between 12.5 and 13.5 mm. It will be understood by those of skill in the art that the separation of the yoke 114 from the tension member 116 during deployment and removal of the yoke 114 upon deployment prevents shed parts in the body. It will also be understood by those of skill in the art that the clipping devices 200-300, as will be described in detail below, have similarly shortened deployment mechanism and capsule lengths which result in a shortened deployed clip length compared to some conventional clips.

Figure 5:
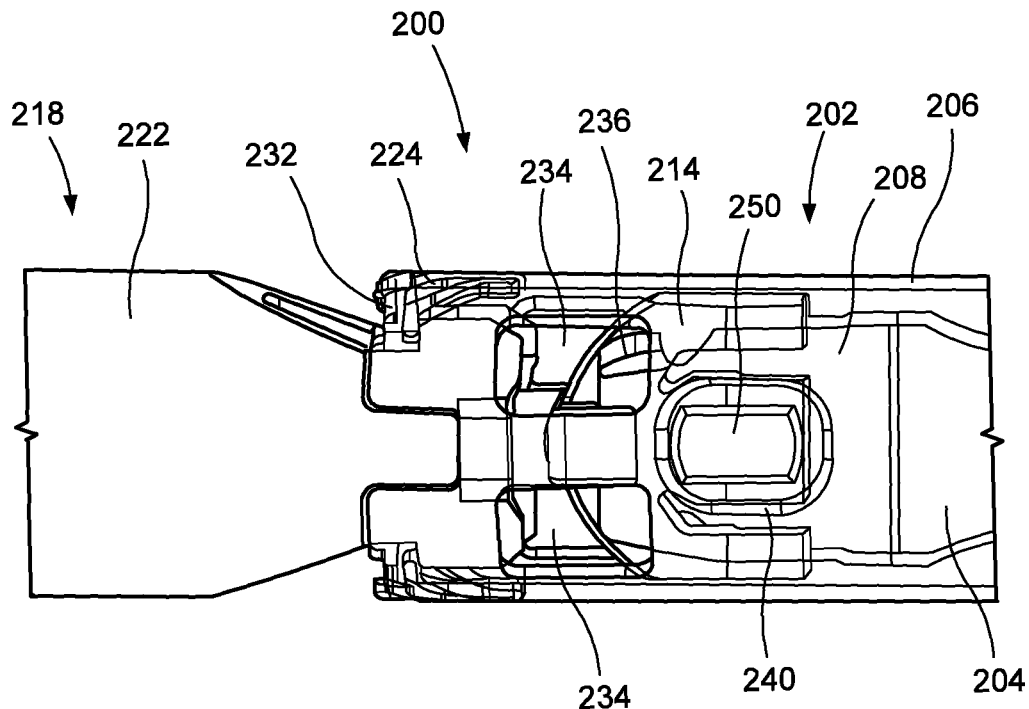
FIG. 5 shows a partially transparent longitudinal side view of a clipping device according to another exemplary embodiment of the present disclosure.
Figure 6:
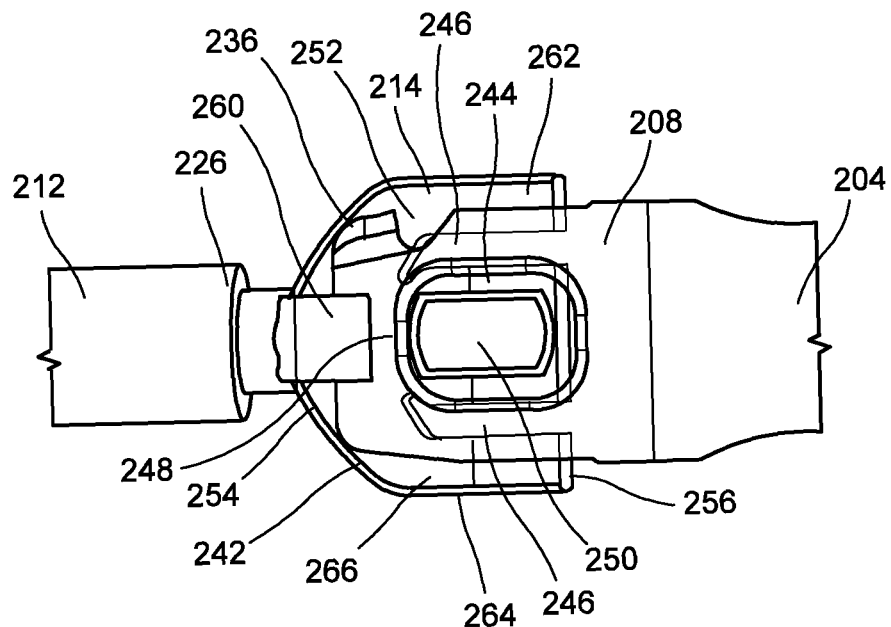
FIG. 6 shows a partially transparent longitudinal side view of a deployment mechanism of the clipping device of FIG. 5.

A clipping device 200 according to another exemplary embodiment, as shown in FIGS. 5-6, is substantially similar to the clipping device 100 described above and comprises a clip 202 including a pair of clip arms 204, proximal ends 208 of which are slidably received within a capsule 206 so that the clip 202 may move between an open configuration, in which distal ends of the clip arms 204 are separated from one another, and a closed configuration, in which distal ends are drawn toward one another. The clip arms 204 are moved between the open and the closed configurations via a control member 212 as described above and the control member 212, a distal end 226 of the control member coupled to a yoke 214.

The capsule 206, the clip arms 204 and a proximal portion 218 of the clipping device 200 to which the capsule 206 is releasably coupled are substantially similar to the corresponding elements of the device 100 described above. Rather than a separate yoke and tension member releasably coupled to one another, however, the clipping device 200 includes a single element—the yoke 214—releasably coupling the control member 212 to the clip arms 204 and maintaining the desired alignment between the clip arms 204.

Similarly to the yoke 114, the yoke 214 includes a central body 252 sized and shaped to be received between the proximal ends 208 of the clip arms 204. The central body 252 extends from a proximal end 254 connected to the distal end 226 of the control member 212 to a distal end 256. The central body 252 is defined via opposing surfaces 262, each opposing surface 262 facing and/or contacting a corresponding one of the clip arms 204. Lateral surfaces 264 connect longitudinal edges 266 of the opposing surfaces 262 from the proximal end 254 to the distal end 256. The yoke 214 also includes an overhang 260 extending distally from the proximal end 255 along each of the opposing surfaces 262 so that a proximal end 208 of each of the clip arms 204 is received between the central body 252 and a corresponding one of the overhangs 260. The overhangs 260 constrain the proximal ends 208 holding them away from the wall of the capsule 206 to prevent locking tabs 236 at the proximal ends 208 of the clip arms 204 from engaging the locking windows 234 of the capsule 206 and locking the clip 202 in the closed configuration until the clip 202 is deployed.

The yoke 214 also includes protrusions 250 extending from opposing surfaces 262 thereof with each protrusion 250 received within a corresponding opening 240 extending through a proximal end 208 of a corresponding one of the clip arms 204 to maintain an alignment therebetween. Thus, in a pre-deployed configuration, the central body 252 is received between the proximal ends 208 with each overhang extending over a corresponding one of the clip arms 204 and each protrusion 250 extending through a corresponding opening 240 of one of the clip arms 204.

The central body 252 also includes a pair of reliefs 246 extending longitudinally along the central body 252 from the distal end 256 along opposing sides of the protrusions 250. The reliefs 246 are sized, shaped and configured to create a stress concentration neck 248 proximal of the protrusions 250 that will break or otherwise disengage or separate during deployment. In particular, when engaging features of the clip arms 204 engage a distal end of the capsule 206, as described above with respect to the clipping device 100, and a predetermined force is exerted on the yoke 214, the yoke 214 will break or separate at the stress concentration neck 248, leaving a first portion 244 of the yoke 214 including the protrusions 250 connected to the clip arms 204, while a remaining proximal portion (second portion 242) is separated therefrom and remains coupled to the control member 212.

Similarly to the yoke 114, a width of the central portion 252 of the yoke 214 substantially corresponds to a width (e.g., diameter) of the capsule 206 so that the central portion 152 is slidable within a channel 230 of the capsule 206 during movement of the clip arms 204 between the open and closed configuration, and facilitates release of the capsule 206 from a bushing 222 of the proximal portion 218 during deployment. In particular, upon separation of the first portion 244 from the second portion 242 at the stress concentration neck 248, the proximal ends 208 of the clip arms 204 are released from the overhangs 260 so that the locking tabs 236 of the clip arms 204 spring outward to engage the locking windows 234 of the capsule 206 locking the clip 202 in the closed configuration.

As the user applies continued proximal force to the control member 212, the second portion 242 is moved proximally past a proximal end 224 of the capsule 206 so that lateral surfaces 264, which define the width of the central portion 252, push inwardly crimped tabs 232 of the capsule 206 radially outward, away from the centerline of the capsule 206, to disengage the capsule 206 from the bushing 222 freeing the clip 202 from the proximal portion of the device 200 so that it may remain in the body clipped over target tissue as the proximal portion of the device 200 is removed from the body. It will be understood by those of skill in the art that the clipping device 200 may be used in a manner substantially similar to the clipping device 100 so that only the clip 202 remains in the body and no parts of the device 200 are shed in the body.

Figure 7:
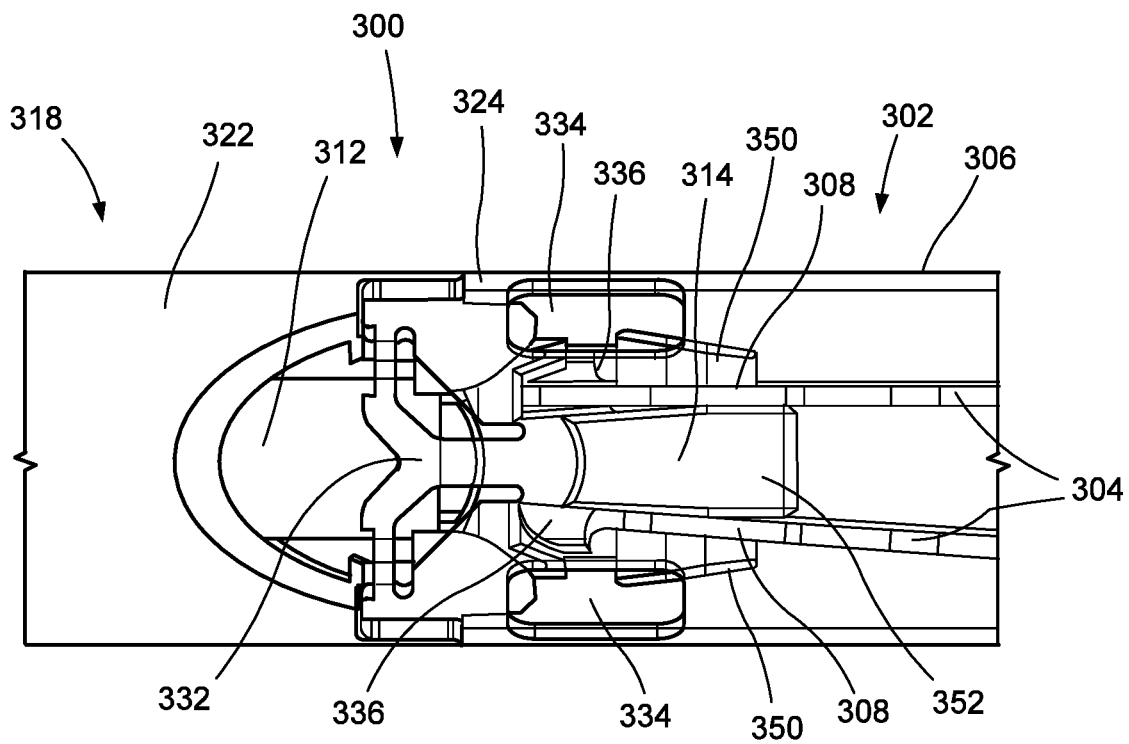
FIG. 7 shows a partially transparent longitudinal side view of a clipping device according to another exemplary embodiment of the present disclosure.
Figure 8:
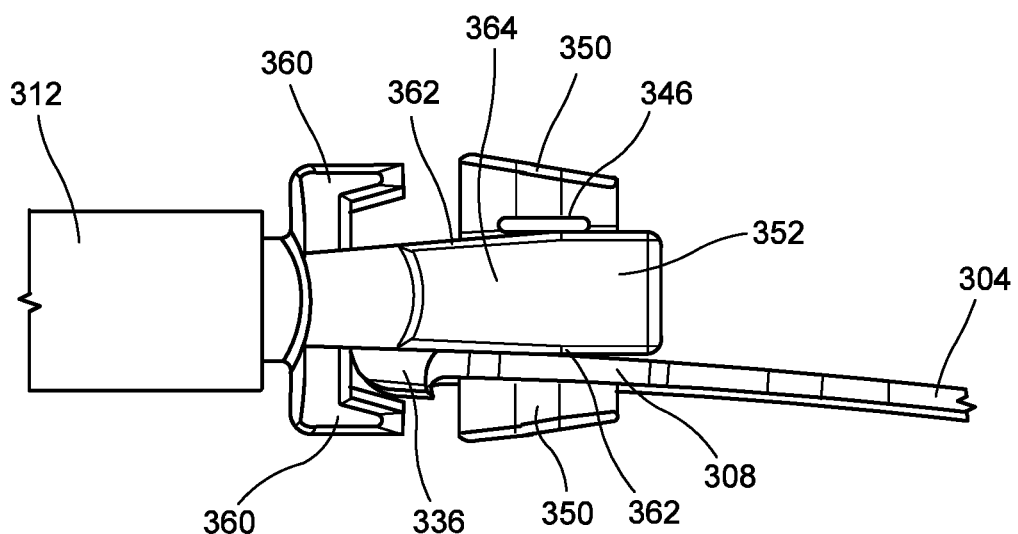
FIG. 8 shows a longitudinal side view of a deployment mechanism of the clipping device of FIG. 7.

As shown in FIGS. 7-8, a clipping device 300 is substantially similar to the clipping device 200, described above, comprising a clip 302 movable between an open configuration and a closed configuration, the clip 302 being releasably coupled to a proximal portion 318 of the device 300 via a separable connection between a bushing 322 at the distal end of the proximal portion 318 and a capsule 306 of the clip 302. The clipping device 300 includes a yoke 314 coupling a control member 312 to a pair of clip arms 304 of the clip 302 for moving the clip arms 304 relative to the capsule 306 to move the clip arms 304 between open and closed configurations as described above.

The yoke 314 also maintains a desired alignment between the clip arms 304. Similarly to the yoke 214, the yoke 314 includes a central portion 352 sized and shaped to be received between proximal ends 308 of the clip arms 304, overhangs 360 constraining the clip arms 304 in an unlocked configuration with the locking tabs 336 at the proximal ends 308 held out of engagement with locking windows 334 of the capsule 306, and protrusions 350 extending from opposing surfaces 362 of the central portion 352 received within openings extending through the proximal ends 308 of the clip arms 304 to maintain a desired alignment therebetween.

The central portion 352 is sized, shaped and configured substantially similarly to the central portion 252 of the clipping device 200. Rather than a pair of reliefs defining a stress neck concentration locating a point of separation between first and second portions of the central portion during deployment, in this embodiment, the yoke 314 includes slots 346 extending through the protrusions 350 reducing a cross-sectional area of the protrusions 350 creating a weakened position at which the protrusions 350 will shear and fail to deploy the clip 302 as will be described in further detail below.

In one embodiment, each of the slots 346 is formed in a portion of the protrusion 350 proximate the opposing surfaces 362 so that, when a predetermined force is exerted thereon, the protrusions 350 are sheared off at this location releasing the proximal ends 308 of the clip arms 304 from the yoke 314. In particular, when target tissue has been gripped between the clip arms 304, as desired, the control member 312 is moved proximally relative to the capsule 306 until engaging features of the clip arms 304 engage the capsule 306 preventing further proximal motion of the clip arms 304 relative to the capsule 306. As the user applies further proximally directed force to the control member 312, the capsule 306 exerts a force on the protrusions 350 until a predetermined force is reached at which the protrusions 350 are sheared off and the proximal ends 308 are released therefrom, freeing the proximal ends 308 of the clip arms 304 to spring radially outward under their natural bias so that locking features of the clip arms 304 engage corresponding locking features of the capsule 306.

For example, the proximal ends 308 spring outward, away from centerline of the capsule 306 so that the locking tabs 336 extending from the proximal ends 308 engage locking windows 334 of the capsule 306. At this point, the yoke 314 is separated from the clip arms 304 and the user draws the control member 312 further proximally until lateral surfaces 364 of the central portion 352, which define a width of the central portion 352, engage inwardly crimped tabs 332 at a proximal end 324 of the capsule 306 to move the tabs 332 radially outward, out of engagement with the bushing 322. It will be understood by those of skill in the art that the clipping device 300 may be used in a manner substantially similar to the clipping devices 100, 200. It will also be understood by those of skill in the art that any shed parts in this embodiment (e.g., sheared off protrusions 350) will remain trapped in the clip 302, preventing the shed parts from interfering with the closed target tissue.

It will be apparent to those skilled in the art that various modifications may be made in the present disclosure, without departing from the scope of the disclosure.

Some embodiments may be described using the expression "coupled" and "connected" along with their derivatives. These terms are not intended as synonyms for each other. For example, some embodiments may be described using the terms "connected" and/or "coupled" to indicate that two or more elements are in direct physical or electrical contact with each other. The term "coupled," however, may also mean that two or more elements are not in direct contact with each other, but yet still co-operate or interact with each other.

As used herein, the singular forms "a," "an," and "the" are intended to include the plural forms as well, unless the context clearly indicates otherwise. It will be further understood that the terms, "comprises" and/or "comprising," or "includes" and/or "including" when used herein, specify the presence of stated features, regions, steps elements and/or components, but do not preclude the presence or addition of one or more other features, regions, integers, steps, operations, elements, components and/or groups thereof.

Furthermore, the Willis "substantial" or "substantially," as well as the terms "approximate" or "approximately," can be used interchangeably in some embodiments, and can be described using any relative measures acceptable by one of skill. For example, these terms can serve as a comparison to a reference parameter, to indicate a deviation that will still provide the intended function. Although non-limiting, the deviation from the reference parameter can be, for example, in an amount of less than 1%, less than 3%, less than 5%, less than 10%, less than 15%, less than 20%, and so on.

Although specific embodiments have been illustrated and described herein, it should be appreciated that any arrangement calculated to achieve the same purpose may be substituted for the specific embodiments shown. This disclosure is intended to cover any and all adaptations or variations of various embodiments. It is to be understood that the above description has been made in an illustrative fashion, and not a restrictive one. Combinations of the above embodiments, and other embodiments not specifically described herein will be apparent to those of skill in the art upon reviewing the above description. Thus, the scope of various embodiments includes any other applications in which the above compositions, structures, and methods are used.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A clipping device, comprising:
a clip including a capsule extending longitudinally from a proximal end to a distal end and including a channel extending therethrough, and a pair of clip arms, proximal ends of which are slidably received within the channel to move the clip arms between an open configuration and a closed configuration;
a bushing releasably coupling the clip to a proximal portion of the device;
a tension member including a distal portion and a proximal portion, each of which are sized and shaped to be received between proximal ends of the clip arms, and a pair of protrusions extending from opposing surfaces of the proximal portion to be received within openings extending through proximal ends of the clip arms to maintain an alignment between the clip arms, the proximal portion including a relief extending longitudinally therealong to define a pair of fingers separated from one another at proximal ends thereof;
a yoke including a central portion sized and shaped to be received between the proximal ends of the clip arms, the central portion including a recess formed at a distal end thereof, the recess sized and shaped to releasably receive the pair of fingers of the tension member, the pair of fingers configured to flex toward one another when a predetermined force is exerted thereon to release the pair of fingers from the recess and disengage the tension member from the yoke during deployment of the clip; and
a control member extending through the proximal portion of the device from a proximal end to a distal end attached to the yoke for moving the clip arms between the open and closed configurations.

2. The device of claim 1, wherein an exterior surface of the pair of fingers are rounded and the recess formed in the central portion is correspondingly rounded so that the pair of fingers are retained within the recess until the predetermined force is exerted thereon.

3. The device of claim 1, wherein the proximal end of the capsule includes tabs biased radially inward to engage a corresponding structure of the bushing, the central portion of the yoke sized and shaped to move the tabs radially outward as the distal end of the control member is moved proximally past the proximal end of the capsule to deploy the clip from the proximal portion.

4. The device of claim 1, wherein the yoke includes a pair of overhangs extending distally from a proximal end of the central portion so that proximal ends of the clip arms are constrained between the central portion and the overhangs toward an unlocked configuration.

5. The device of claim 4, wherein the proximal ends of the clip arms are biased radially outward so that, in the unlocked configuration, locking structures at the proximal ends of the clip arms are prevented from engaging corresponding locking features of the capsule.

6. The device of claim 5, wherein the locking structures include locking tabs extending from proximal ends of the clip arms and the locking features of the capsule including windows extending laterally through a wall thereof so that, when the proximal ends of the clip are released from the distal end of the control member, the locking tabs are received within the locking windows to lock the clip in the closed configuration.

7. The device of claim 1, wherein the clip arms include engaging features configured to engage portion of the capsule such that, when the engaging features engage the capsule, the clip arms are prevented from moving further proximally relative to capsule and the predetermined force is exerted on the distal end of the control member.

8. A clipping device, comprising:
a clip including a capsule extending longitudinally from a proximal end to a distal end and including a channel extending therethrough, and a pair of clip arms, proximal ends of which are slidably received within the channel to move the clip arms between an open configuration and a closed configuration;
a bushing releasably coupling the clip to a proximal portion of the device;

a control member extending through the proximal portion of the device from a proximal end to a distal end releasably coupled to the clip arms to move the clip between the open and closed configurations; and a yoke attached to the distal end of the control member for releasably coupling the control member to the clip arms, the yoke including a central portion sized and shaped to be received between proximal ends of the clip arms, a pair of protrusions extending from opposing surfaces of the central portion to be received within openings extending through the proximal ends of the clip arms to maintain an alignment therebetween, and a pair of reliefs formed therein so that, when a predetermined force is exerted on the yoke, a portion of the yoke defined via the reliefs is separated from a remaining portion of the yoke to release the clip arms from the control member during deployment of the clip, wherein the proximal end of the capsule includes tabs biased radially inward to engage a corresponding structure of the bushing, the central portion of the yoke sized and shaped to move the tabs radially outward as the distal end of the control member is moved proximally past the proximal end of the capsule to deploy the clip from the proximal portion.

9. The device of claim 8, wherein the pair of reliefs extend from the distal end of the central portion of the yoke along opposing sides of the protrusions to define a stress concentration neck along which the yoke is configured to separate during deployment of the clip.

10. The device of claim 8, wherein the pair of reliefs extend through the protrusions proximate the opposing surfaces of the central portion so that, when the predetermined force is exerted thereon, the protrusions are sheared off to release the clip arms from the control member.

11. The device of claim 8, wherein the yoke includes a pair of overhangs extending distally from a proximal end of the central portion so that proximal ends of the clip arms are constrained between the central portion and the overhangs toward an unlocked configuration.

12. The device of claim 11, wherein the proximal ends of the clip arms are biased radially outward so that, in the unlocked configuration, locking structures at the proximal ends of the clip arms are prevented from engaging corresponding locking features of the capsule.

13. The device of claim 12, wherein the locking structures include locking tabs extending from proximal ends of the clip arms and the locking features of the capsule including windows extending laterally through a wall thereof so that, when the proximal ends of the clip are released from the distal end of the control member, the locking tabs are received within the locking windows to lock the clip in the closed configuration.

14. The device of claim 8, wherein the clip arms include engaging features configured to engage portion of the capsule such that, when the engaging features engage the capsule, the clip arms are prevented from moving further proximally relative to capsule and the predetermined force is exerted on the distal end of the control member.

15. A method for treating target tissue, comprising:
inserting a clip device through a working channel of an endoscope to a target site within a body until a clip of the clip device extends distally past a distal end of the working channel, the clip device including a capsule and a pair of clip arms slidably received therein, the pair of clip arms aligned relative to one another via a tension member including a distal portion and a proximal portion sized and shaped to be received between proximal ends of the clip arms, and a pair of protrusions extending from opposing surfaces of the proximal portion to be received within openings extending through proximal ends of the clip arms to maintain an alignment between the clip arms;

moving the clip device between an open configuration and a closed configuration via a control wire coupled to the clip arms, until selected target tissue is received between the distal ends, a distal end of the control wire coupled to proximal ends of the clip arms via a yoke including a central portion received between the proximal ends of the clip arms, a pair of fingers of the proximal portion of the tension member releasably received within a recess of the central portion;

drawing the clip arms proximally into the capsule to move the clip toward the closed configuration to grip the target tissue between the clip arms; and deploying the clip from a proximal portion of the clip device by drawing the control member proximally relative to the capsule until a predetermined force is exerted on the pair of fingers via the yoke, causing the pair of fingers to flex toward one another to release the tension member from the yoke.

16. The method of claim 15, wherein deploying the clip includes moving the distal end of the control member proximally past the proximal end of the capsule, which includes tabs crimped radially inward to engage a portion of the proximal portion of the clip device, so that the central portion of the yoke moves the tabs radially outward to disengage the proximal portion.

17. The method of claim 15, wherein deploying the clip includes releasing proximal ends of the clip arms from between a pair of overhangs extending distally from a proximal end of the central portion and the central portion.

18. The method of claim 17, wherein the pair of overhangs constrain outwardly biased proximal ends of the clip arms toward an unlocked configuration, in which proximal ends are constrained toward the central portion.

19. The method of claim 17, wherein, when the proximal ends of the clip arms are released from the pair of overhangs, the proximal ends of the clip arms revert to their biased configuration so that locking structures at the proximal ends of the clip arms engage corresponding locking features of the capsule to lock the clip in the closed configuration.

* * * * *